Dec. 3, 1935. R. L. CATRON Plant Pat. 157
ROSE
Filed March 15, 1935
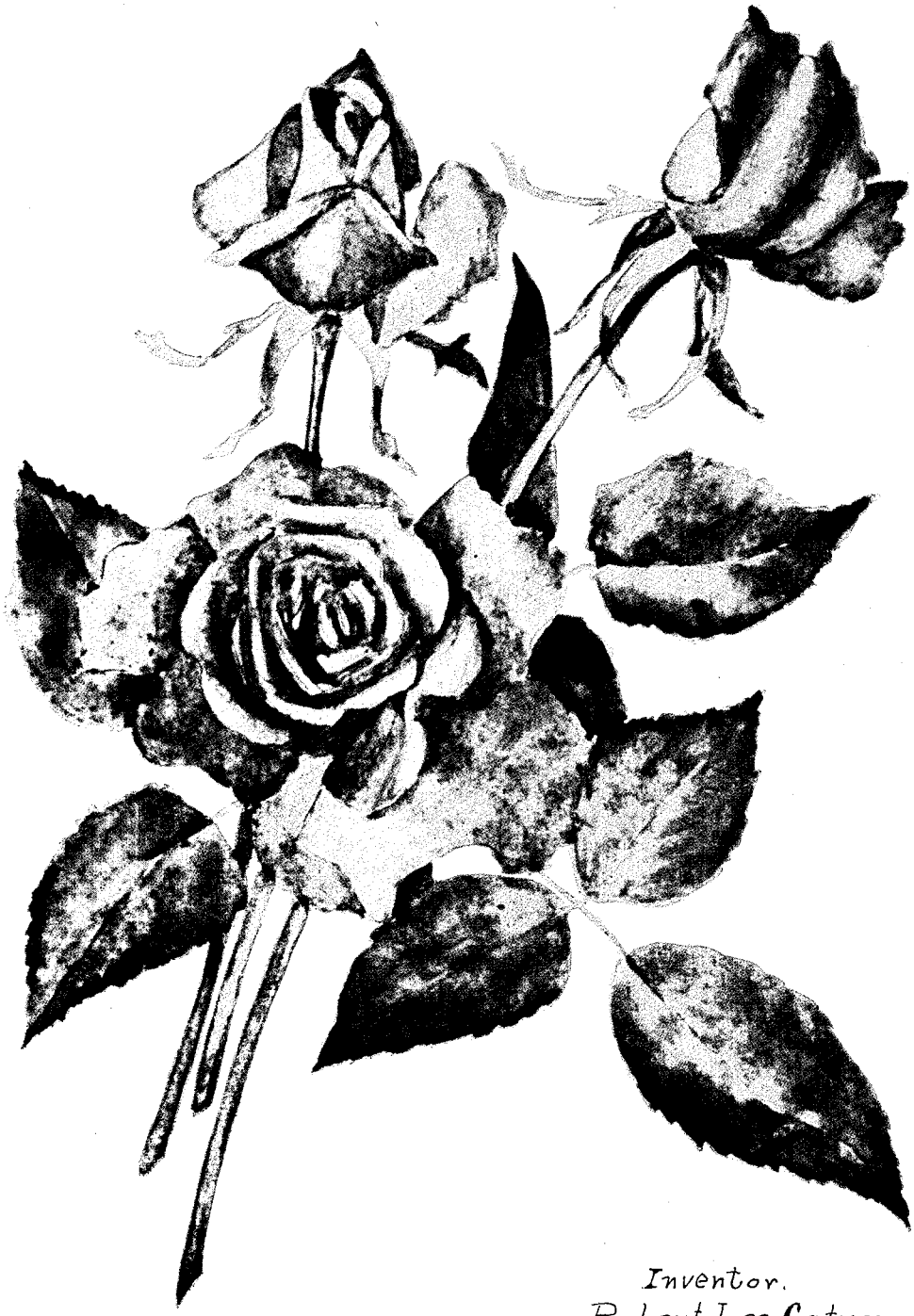
Inventor.
Robert Lee Catron;
By Robert W. Randle,
Attorney.

Patented Dec. 3, 1935

Plant Pat. 157

UNITED STATES PATENT OFFICE

157

ROSE

Robert Lee Catron, Richmond, Ind., assignor to Joseph H. Hill Company, Richmond, Ind., a corporation of Indiana Application March 15, 1935, Serial No. 11,295

1 Claim. (Cl. 47—61)

This application relates to the discovery, development, and production of a new variety of rose, which was discovered in the greenhouses of the Joseph H. Hill Company, in Richmond, Indiana, where it originated as a sport from a roseplant known by the trade name of "Better Times", patented August 23rd, 1932, by this applicant, and it is identified as Rose Patent No. 23.

The grandparent of my new rose is known by the name of "Briarcliff", and it is not patented.

The subject of this application was discovered, by your applicant, on November 14th, 1934, as a sport of said parent plant, after which I immediately took the proper steps to reproduce it, which I did asexually, by budding which, about January 8th, 1935, produced a replica of the original sport above mentioned.

This latter rose was immediately budded, and on March 4th, 1935, it also came true in every respect to its parent. Said second product was then budded, and on May 10th, 1935, it also came true in every respect with relation to its parent and said sport. Other roses, based on the above, are now being produced, at the same place, which appear to be replicas of said sport and its said descendants.

In view of the above I believe that the subject of this application is now permanently fixed as a new variety.

The buds of my new rose are large and long, and each tapers to a point at its outer terminal, and each being enclosed by its large, light green colored calyx.

The petals of my new rose are of very large size, with the edges thereof irregular, or escalloped, with the outer portion inclined to curve downwardly, as the bloom becomes fully developed, thereby further increasing the apparent volume of the bloom as an entirety.

The face or upper or inner sides of the major portion of the petals present a bright velvety scarlet carmine color, while the reverse or outer sides are the same, except that they present a lighter tinge in the color, as compared with the inner side. The color of the major portion of the inner side of the petals is most nearly represented on Plate I of Ridgeways color chart, under the title "Carmine," but this comparison fails to show the "bright velvety scarlet" which the bloom presents in this instance. This color is somewhat like that of fresh human blood, or of unfurling petals of Etoile de Hollande rose. The color is very slow to fade, in spite of long exposure to sunlight.

The minor inner portions of both sides of the petals are white with a slight yellowish tinge, similar to but slightly lighter than that shown at the outer edges of the outer petals of the fully opened bloom in Plant Patent No. 80 as published. These portions are at and near the base or stalk or petiole of the petal, as in Plant Patents 2, 21 and 91 and in Etoile de Hollande.

The color of the central portion of each bloom, that is the corona, when the bloom is fully opened, is of a dark yellowish color, somewhat darker than that shown by said "Better Times" rose, the same being produced, to a great extent, by the dark yellowish color of the stigmas and the other elements of the generative organs of the bloom.

All of said features combined form a very attractive ensemble to the rose plant as an entirety.

The bloom, and the bush, is of quick, vigorous, and gorgeous growth, which persists until its maturity, and it is of long duration after it has fully matured.

The bloom, and the bush as a whole, have no indication of disease, or deformity, and no other deleterious interference has been found associated therewith.

The stems, and the bush as a whole, are not permitted to grow longer than five or six feet in height, and they are very strong and are symmetrical and almost vertical in extent.

It has been demonstrated that this new variety of rose is remontant, as a new crop of bloom develops every seven or eight weeks throughout the year; usually with but one bloom to each peduncle, and with 38 to 40 petals to each bloom.

The bloom of this rose is very large, measuring when fully opened, five and frequently six inches in diameter and as a whole they appear globular. The bloom of this rose dispenses a sweet spicy inimitable fragrance, similar to but more intensive and pleasant than that mentioned in Plant Patent No. 21.

The sepals are large and regular, tapering gradually to near the apex thereof, after which the outline thereof is obtuse and terminating in a pointed tip. As the bud opens the sepals turn back to their respective peduncles and later they are almost hidden by the petals.

This rose plant, as an entirety, is classed as a bush, and as such it has no particular characteristic other than that stated above, with the exception that the stems are practically free of spines, or prickles, except near the ground, but where they do develop they are soft and unoffensive.

The foliage is abundant, usually in groups of three leaflets nearest the bloom, and five further down. The leaflets are of a dark green color, oval in shape, and pointed at their outer portion.

Perhaps the two most important features of my new rose reside in its combination of colors, and the majesty of appearance as an entirety.

All descriptive features not herein set forth are to be considered as substantially the same as those of the parent and the grandparent of the rose herein described.

Having now described my new rose, what I claim is:

A new variety of rose which eventuated as a sport, which after being asexually reproduced, presents very large and long buds each tapering to a point at its outer terminus; said rose being characterized particularly, when the bloom is fully opened, by the major outer portion of the inner sides of the petals presenting very bright velvety scarlet carmine color, with the outer sides of the petals the same as the inner sides except that the outer major portion thereof are lighter in color and without the velvety appearance, but appearing more glossy than the inner side thereof; the slowness of the bloom to fade; the very large size of the bloom; the combination of color-shades presented by the bloom; the sweet spicy fragrance of the bloom; the remontant character of the plant; its comparative freedom from spines; and the majesty and beauty thereof as an entirety.

ROBERT LEE CATRON.